United States Patent [19]

Friebe et al.

[11] 4,378,363
[45] Mar. 29, 1983

[54] CERTAIN HETEROCYCLIC-CARBOXAMIDO-PHENOXY-AMINOPROPANOLS, COMPOSITIONS CONTAINING SAME AND METHODS OF USING SAME

[75] Inventors: Walter-Gunar Friebe, Darmstadt; Wolfgang Kampe, Heddesheim; Wolfgang Bartsch, Viernheim; Gisbert Sponer, Hemsbach; Karl Dietmann, Mannheim, all of Fed. Rep. of Germany

[73] Assignee: Boehringer Mannheim GmbH, Mannheim-Waldhof, Fed. Rep. of Germany

[21] Appl. No.: 207,527

[22] Filed: Nov. 17, 1980

[30] Foreign Application Priority Data

Nov. 29, 1979 [DE] Fed. Rep. of Germany ....... 2948056

[51] Int. Cl.³ .................. C07D 209/42; C07D 213/81; A61K 31/455; A61K 31/40
[52] U.S. Cl. .................................... 424/266; 424/274; 546/316; 548/495; 548/537
[58] Field of Search ............... 546/316; 260/326.14 R, 260/326.47; 424/266, 274; 548/495, 537

[56] References Cited

U.S. PATENT DOCUMENTS 4,278,680 7/1981 Hubner et al. ..................... 424/266

Primary Examiner—Alan L. Rotman
Attorney, Agent, or Firm—Felfe & Lynch

[57] ABSTRACT

This invention relates to new aminopropanol compounds having beta-adrenergic activity. In addition, the invention is directed to pharmaceutical compositions containing such compounds for the treatment of cardiac and circulatory infirmities and to methods for treating such infirmities.

More particularly, the invention relates to new aminopropanol compound of the formula

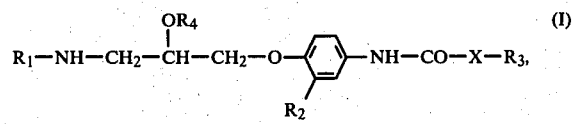

wherein
$R_1$ is a low alkyl moiety, which can be substituted, if desired, by a group $Z-R_5$;
$R_2$ is hydrogen or a low alkanoyl group;
$R_3$ is a mono- or bicyclic heterocyclic compound having 1 to 2 hetero atoms, which can be mono- or polysubstituted, if desired, by halogen, amino, hydroxyl, low alkoxyl, low alkyl;
$R_4$ is hydrogen, a low alkanoyl group or an aroyl group;
$R_5$ is hydrogen or a carbocyclic or heterocyclic aryl moiety, which can be mono- or polysubstituted, if desired, by hydroxyl, low alkyl, low alkenyl, low alkoxyl or low alkenyloxyl;
X is a valence bond or a methylene group; and
Z is a valence bond, an oxygen atom, or a sulfur atom, and their pharmacologically compatible salts.

21 Claims, No Drawings

CERTAIN HETEROCYCLIC-CARBOXAMIDO-PHENOXY-AMINOPROPANOLS, COMPOSITIONS CONTAINING SAME AND METHODS OF USING SAME

BACKGROUND OF THE INVENTION

Since the compounds of Formula I have asymmetrical carbon atoms, the optically active forms and racemic mixtures of these compounds are also subject matter of the invention. Since the compounds of Formula I contain groups capable of tautometry, all tautomeric forms of these compounds are also subject matter of the invention.

It is known that 1-amino-3-aryloxy-2-propanol derivatives have a beta-adrenergic blocking activity. In Netherlands Patent No. 68.18289, derivatives are described which have aliphatic moieties $R_3$; German Patent No. 1,493,887 and British Patent No. 1,185,046 claim substances having aliphatic and carboxyclic moieties $R_3$. One prominent representative of these compounds, practolol, has meantime proved to be toxic and has had to be withdrawn from the market.

Compounds having heterocyclic moieties $R_3$ have never previously become known. The use of these moieties produces a surprising intensification of action, and brings it about that the substances thus far have shown no practolol-like toxicity.

The term, "a low alkyl group" of the substituents $R_1$, $R_3$ and $R_5$, as used herein, is to be understood to refer to straight-chain or branched groups having one to six, preferably one to four carbon atoms, such as, for example, methyl, ethyl, propyl, isopropyl, butyl, isobutyl, sec. butyl, tert. butyl or n-hexyl.

Alkanoyl groups of substituents $R_2$ and $R_4$ contain one to eight, preferably one to five carbon atoms, and their alkyl groups can be straight-chain, branched or cyclic. The acetyl moiety and the pivaloyl moiety are preferred.

The term, "aroyl group" of substituent $R_4$, is to be understood to refer to a benzoyl or a naphthoyl group.

Alkoxy groups of substituents $R_3$ and $R_5$ contain one to six, preferably one to four carbon atoms, examples being the methoxy, ethoxy, propoxy, butoxy or pentoxy group. The methoxy, ethoxy and propoxy groups are preferred.

Halogen, in the meaning of the invention, is to be understood to refer to fluorine, chlorine, bromine and iodine, especially fluorine, chlorine and bromine.

The term, "heterocyclic moieties" of substituents $R_3$ and $R_5$, is to be understood to mean monocyclic and bicyclic compounds consisting of five- and/or six-member rings having one or two hetero atoms. Nitrogen, oxygen and sulfur can be the hetero atoms. The heteroxyclics can be unsaturated, saturated or partially unsaturated. The pyrrolyl, pyrrolinyl, pyridyl, pyrazinyl, thiazolyl, indolyl, tetrahydroindolyl, quinolinyl, benzofuranyl and benzimidazolyl moieties are preferred.

Carbocyclic aryl moieties can be phenyl or naphthyl moieties, the phenyl moiety being especially preferred.

The preparation of the new compounds of the general Formula I is characterized either by reacting, in a known manner, (a) a compound of Formula II

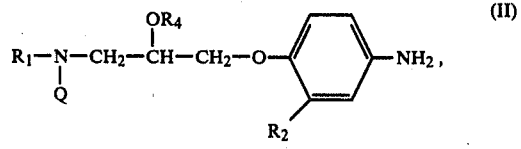

wherein $R_1$, $R_2$ and $R_4$ have the meaning given above, and Q represents hydrogen or a protective group with a compound of Formula III $$Y-CO-X-R_3 \quad (III),$$

wherein X and $R_3$ have the meaning given above and Y represents a reactive moiety, or (b) by reacting a compound of Formula IV

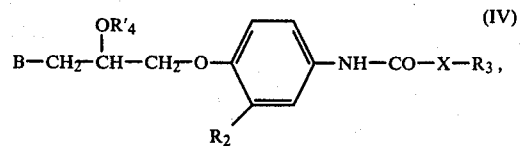

wherein $R_2$, $R_3$ and X have the same meaning as above, B represents a reactive group, and $R_4'$ has the same meaning as $R_4$ or together with B represents a valence line, with a compound of Formula V $$R_1NH-Q \quad (V),$$

wherein $R_1$ and Q have the meaning given above, or (c) by reacting a compound of Formula VI

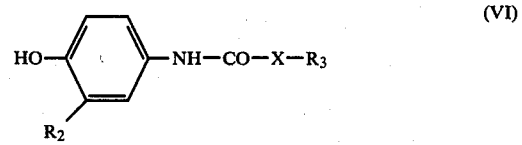

wherein $R_2$, $R_3$ and X have the same meaning as above, with a compound of Formula VII

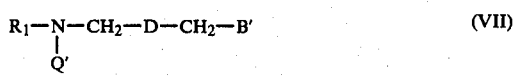

wherein
$R_1$ has the same meaning as above,
B' represents a reactive group,
D represents a CO- or CH-OR$_4''$ group, $R_4''$ having the same meaning as $R_4$ given above or representing together with B' a valence line, and
Q' has the same meaning given above for Q or, together with B', can be a single bond, and, if D represents the CO group, then reducing the product, splitting off, if desired, a protective group representing Q or Q', transforming afterwards, if desired, one moiety $R_4$ in a product compound of the general Formula I, by conventional methods, to another moiety $R_4$ defined by the claim, and converting the obtained compounds, if desired, to their pharmacologically compatible salts.

Protective groups representing Q or Q' in compounds of Formulas II, V and VII can be moieties which can be split off by hydrolysis or hydrogenolysis, such as for example low alkanoyl, aroyl, arylmethyl, diarylmethyl or triarylmethyl moieties. The benzyl moiety is preferred.

Reactive moieties Y in compounds of the general Formula III can be any moieties which are used in peptide chemistry for the activation of carboxylic acids, such as for example halogen atoms, the azido group, alkyloxy groups, aryloxy groups and acyloxy groups.

Reactive groups B in compounds of the general formula IV, and B' in compounds of general formula VII, are especially acid moieties, for example those of hydrogen halide acids and sulfonic acids. Chlorides, mesyloxy and tosyloxy moieties are especially preferred.

The methods of the invention are best performed in a solvent that is inert under the conditions of the reaction, such as water, methanol, ethanol, n-butanol, dioxane, dimethylformamide, hexamethylphosphoric acid triamide, or ethylene glycol dimethyl ether, in the presence, if desired, of an acid-binding agent. The reactions can also be achieved by mixing the components of the reaction without solvent. The reactions are performed at room temperature or with heating, under a protective gas atmosphere if necessary.

The reduction of the group CO representing D, if it is to be performed, is best carried out by catalytic hydrogenation with noble metal or nickel catalysts, or by means of complex metal hydrides such as sodium borohydride.

The starting compounds used in the method of the invention are, as a rule, compounds known in the literature. New compounds are generally obtained in a manner similar to the method described for the preparation of these known compounds.

An example of a transformation of a substituent $R_4$, to be performed after the principal reaction in some cases, is the acylation of an OH group to an alkanoyloxy or aroyloxy group. The esterification can be accomplished in a conventional manner by reaction with an acid halide or acid anhydride, in the presence, if desired, of an acid-binding agent such as pyridine or triethylamine, for example.

The splitting off of an arylmethyl, diarylmethyl or triarylmethyl group representing Q or Q' is performed, for example by hydrogenation in the presence of noble metal catalysts.

For the conversion of the compounds of Formula I to their pharmacologically acceptable salts, they are reacted, preferably in an organic solvent, with an inorganic or organic acid, such as hydrochloric acid, hydrobromic acid, phosphoric acid, sulfuric acid, acetic acid, lactic acid, citric acid, maleic acid or benzoic acid.

The compounds of Formula I pursuant to the invention can be produced in the form of a racemic mixture. The separation of the racemate into the optically active forms is accomplished through the diastereomeric salts, by methods known in themselves. Tartaric acid, malic acid, camphoric acid and camphorsulfonic acid can chiefly be used as active acids.

For the preparation of pharmaceutical products, the compounds of Formula I are mixed in a known manner with suitable pharmaceutical vehicles, flavoring agents, aromatic substances and dyes, and formed, for example, into tablets or dragees, or they are suspended or dissolved in water or oil, such as olive oil, with the addition of appropriate adjuvants.

The new compounds of Formula I pursuant to the invention and their salts can be administered enterally or parenterally in liquid or solid form. As the medium for injectables, water is used preferentially, and contains the additives commonly used in injectable solutions, such as stabilizers, solubilizers or buffers. Examples of such additives are tartrate and citrate buffers, ethanol, complexing agents (such as ethylene diamine tetraacetic acid and its non-toxic salts), and polymers of high molecular weight (such as liquid polyethylene oxide) to control viscosity. Examples of solid vehicles are starch, lactose, mannitol, methyl cellulose, talc, highly disperse silicic acids, fatty acids of higher molecular weight (such as stearic acid), gelatines, agar-agar, calcium phosphate, magnesium stearate, animal and vegetable fats and solid high polymers (such as polyethylene glycols); preparations suitable for oral administration can contain flavoring agents and sweeteners, if desired.

The dosage used will depend on the age, state of health and body weight of the patient, the severity of the illness, other treatment simultaneously administered, the frequency of the treatments, and the kind of action desired. Usually the daily dose of the active compounds amounts to from 0.1 to 50 milligrams per kilogram of body weight. Normally, 0.5 to 40, and preferably 1.0 to 20 mg/kg/day in one or more doses per day are effective in obtaining the desired results.

The following experiments were performed for the detection of the beta-adrenergic blocking activity:

Record of Experiment

Rabbits are fixed in wood cages and their pulse is derived through needle electrodes and displayed in a frequency counter (measuring time 15 sec). First, 1 microgram per kilogram of isoprenalin was injected through a vein in the ear; which increase the pulse rate from about 210 to about 350 beats per minute. Then the dissolved test substances were administered intravenously at ten-minute intervals $(0.125+0.125+0.250+0.500+1.0+2.0+4.0$ mg/kg i.v.), and the pulse was read again after the administration of the isoprenalin. The inhibition of the tachycardia produced by isoprenalin is to be considered as a measure of the beta blocking. The dose of the test substances which reduces the pulse rate increase due to isoprenalin (1 $\mu$g/kg i.v.) by 30% ($HD_{30}$) was interpolated.

The reference substance used was practolol (formerly sold as Dalzic ®, a known beta-blocking agent of chemically similar structure.

The results are given in Table I.

TABLE I

| Substance | $HD_{30}$* ($\mu$g/kg i.v.) |
| --- | --- |
| Practolol | 1320 |
| Example 1 | 469 |
| Example 3 | 777 |
| Example 2a | 1124 |
| Example 2b | 3413 |
| Example 2c | 2093 |
| Example 2d | 824 |
| Example 4 | 1761 |
| Example 2e | 308 |
| Example 7 | 1454 |
| Example 2f | 7697 |
| Example 8a | 3549 |
| Example 8b | 1676 |
| Example 2g | greater than 8000 |

*$HD_{30}$ = Index of the beta-blocking activity, namely the dose which produces a 30% reduction of the pulse rate increase under 1 $\mu$g/kg i.v. of isoprenalin.

In addition to the compounds described in the following examples, the following are furthermore preferred in the meaning of the present patent application:

1-[4-(2-amino-thiazole-4-carboxamido)phenoxy]-3-isopropylamino-2-propanol
1-isopropylamino-3-[4-(5-methyl-pyrazine-2-carboxamido) phenoxy]-2-propanol
1-[4-(indole-2-carboxamido)phenoxy]-3-[2-(2-methoxyphenylthio)ethylamino]-2-propanol
1-[2-(2-allyloxy-phenoxy-propylamino]-3-[4-(indole-2-carboxamido)phenoxy]-2-propanol

EXAMPLES

The following examples indicate a few of the many variants of the method, which can be used for the synthesis of the compounds of the invention, and one is an example of the preparation of tablets. However, they are not to be considered as a limitation of the subject matter of the invention.

Example 1
1-[4-(indole-2-carboxamido)phenoxy]-3-isopropylamino-2-propanol hydrochloride A solution of 13.4 grams of indole-2-carbonylchloride in 50 ml of dichloromethane is added drop by drop to a mixture of 18.8 g of 1-(4-amino-phenoxy)-3-N-benzylisopropylamino-2-propanol, 33.5 grams of sodium hydrogen carbonate and 200 ml of dichloromethane, the mixture is refluxed for five hours, dilute caustic soda solution is added, the organic phase is separated and concentrated, and the residue is dissolved with ether. 17.6 grams of 1-[4-(indole-2-carboxamido)phenoxy]-3-N-benzylisopropylamino-2-propanol remain, having a melting point of 173°–175° C.

The above compound is dissolved in methanol, ethereal hydrochloric acid solution is added, the mixture is concentrated, the residue is dissolved in 200 milliliters of 90% methanol, and hydrogenated at room temperature and one bar of hydrogen pressure over two grams of 10% palladium charcoal. After the calculated amount of hydrogen has been absorbed, filtration is performed, the solution is concentrated, and the residue is recrystallized from ethanol. 12.5 grams of the above compound are obtained (48% of the theory), having a melting point of 247°–249° C.

Example 2

The following are obtained in a manner similar to that described in Example 1:

| Name of compound | Yield % | Melting Point °C. (Solvent) |
|---|---|---|
| (a) 1-[2-(3,4-dimethoxy-phenyl)ethylamino]-3-[4-(indole-2-carboxamido)phenoxy]-2-propanol hydrochloride from | 62 | 222–223 (methanol) |
| 1-(4-amino-phenoxy)-3-[N—benzyl-2-(3,4-dimethoxyphenyl)ethylamino]-2-propanol and indole-2-carbonyl chloride | | |
| (b) 1-[4-(indole-2-carboxamido)-phenoxy]-3-[2-(2-methoxyphenoxy)-ethylamino]-2-propanol hydrochloride from | 57 | 160–162 (methanol) |
| 1-(4-amino-phenoxy)-3-[N—benzyl-2-(2-methoxyphenoxy)ethylamino]-2-propanol and indole-2-carbonyl chloride | | |
| (c) 1-[4-(indole-2-carboxamido)phenoxy]-3-[(+)-(S)-1-methyl-propyl-amino]-2-propanol hydrochloride from | 50 | 216–217 (ethanol/ether) |
| 1-(4-amino-phenoxy)-3-[(+)-(S)-N—benzyl-1-methypropylamino]-2-propanol and indole-2-carbonyl chloride | | |
| (d) 1-isopropylamino-3-(4-nicotinoylamido-phenoxy)-2-propanol hydrochloride from | 86 | 227–228 (methanol/ether) |
| 1-(4-aminophenoxy)-3-N—benzyl-isopropylamino-2-propanol and nicotinoyl chloride | | |
| (e) 1-isopropylamino-3-[4-(pyrrole-2-carboxamido)phenoxy]-2-propanol from | 59 | 177–178 (acetic ester) |
| 1-(4-aminophenoxy)-3-N—benzyl-isopropylamino-2-propanol and pyrrole-2-carbonyl chloride | | |
| (f) 1-[4-(5-n-butyl-pyridine-2-carboxamido)phenoxy]-3-isopropylamino-2-propanol hydrochloride from | 89 | 160–162 (isopropanol) |
| 1-(4-aminophenoxy)-3-N—benzyl-isopropylamino-2-propanol and 5-n-butylpyridine-2-carbonyl chloride | | |
| (g) 1-[4-(2-hydroxypyridine-3-carboxamido)phenoxy]-3-isopropylamino-2-propanol hydrochloride from | 50 | 275–276 (methanol) |
| 1-(4-aminophenoxy)-3-N—benzyl-isopropylamino-2-propanol and 2-hydroxynicotinoyl chloride | | |
| (h) 1-t-butylamino-3-[4-(indole-2-carboxamido)phenoxy]-2-propanol hydrochloride from | 54 | 268–270 (methanol) |
| 1-(4-aminophenoxy)-3-N—benzyl-t-butylamino-2-propanol and indole-2-carbonyl chloride | | |

Example 3
1-[4-(indole-3-acetamido)phenoxy]-3-isopropylamino-2-propanol

A mixture of 8.75 g of indole-3-acetic acid, 7 ml of triethylamine, 150 ml of dioxane and 75 ml of acetone is refluxed for 10 minutes, chilled to −5° C., and a solution of 13 ml of chloroformic acid isobutyl ester in 60 ml of dioxane and 30 ml of acetone is added. After ten minutes of stirring, a solution of 15.7 g of 1-(4-aminophenoxy)-3-N-benzylisopropylamino-2-propanol and 7 ml of triethylamine in 40 ml of water, 40 ml of dioxane and 20 ml of acetone is added drop by drop, the mixture is stirred for 15 minutes at 0° C., poured into water and extracted with dichloromethane. The extract is concentrated and purified by column chromatography on silica gel, the eluent being a mixture of dichloromethane and methanol in a ratio of 97:3.

9.8 grams of 1-[4-(indole-3-acetamido)phenoxy]-3-N-benzylisopropylamino-2-propanol are isolated, and debenzylated by hydrogenolysis as described in Example 1.

After conversion to the free base and recrystallization from a mixture of acetic ester and ether, 6.0 grams of the title compound remain, or 32% of the theory, having a melting point of 137°–138° C.

Example 4
1-isopropylamino-3-[4-(4,5-dihydro-2-hydroxypyrrole-1-acetamido)phenoxy]-2-propanol A mixture of 9.3 g of 1-(4-aminophenoxy)-3-N-benzylisopropylamino-2-propanol and 6.0 g of 4,5-dihydro-2-hydroxypyrrole-1-acetic acid ethyl ester is heated for 16 hours at 100° C., and then purified by column chromatography on silica gel, using a 19:1 mixture of dichloromethane and methanol as the eluent.

9.5 grams of 1-N-benzylisopropylamino-3-[4-(4,5-dihydro-2-hydroxypyrrole-1-acetamido)phenoxy]-2-propanol are isolated, which are debenzylated by hydrogenolysis in a solvent mixture of 100 ml of methanol and 100 ml of tetrahydrofuran, at one bar of hydrogen pressure over one gram of 10% palladium charcoal.

After filtration, concentration and recrystallization from a mixture of isopropanol and ether, 5.2 grams of the title compound remain (49% of the theory), having a melting point of 123°–124° C.

Example 5
1-[4-(indole-2-carboxamido)phenoxy]-3-isopropylamino-2-propanol

A solution of 13.5 grams if indole-2-carbonyl chloride in 50 ml of acetone and dilute soda lye are added simultaneously, drop by drop, to a solution of 11.1 grams of 1-(4-aminophenoxy)-3-isopropylamino-2-propanol in 200 ml of 50% aqueous acetone at pH 4 to 5, so that the pH of the solution is maintained between 4 and 5. After one hour of stirring at room temperature, the solution is adjusted with soda lye to pH 11 to 12 and filtered. After washing with acetone and ether, 16.3 grams of the title compound (89% of the theory) are isolated, with a melting point of 208° to 210° C.

Example 6

The following substances are obtained in a manner similar to that described in Example 5:

| | Name of compound | Yield % | Melting Point °C. (Solvent) |
|---|---|---|---|
| (a) | 1-[4-(indole-3-carboxyamido)-phenoxy]-3-isopropylamino-2-propanol from 1-(4-aminophenoxy)-3-isopropylamino-2-propanol and indole-3-carbonyl chloride | | |
| (b) | 1-[4-(benzofuran-2-carboxamido)-phenoxy]-3-isopropylamino-2-propanol from 1-(4-aminophenoxy)-3-isopropylamino-2-propanol and benzofuran-2-carbonyl chloride | 74 | 145–147 (isopropanol) |
| (c) | 1-[4-(5-fluorindole-2-carboxamido)-phenoxy]-3-isopropylamino-2-propanol from 1-(4-aminophenoxy)-3-isopropylamino-2-propanol and 5-fluor-indole-2-carbonyl chloride | 68 | 195–197 (isopropanol) |
| (d) | 1-[4-(4-hydroxyindole-2-carboxamido)phenoxy]-3-isopropylamino-2-propanol from 1-(4-aminophenoxy)-3-isopropylamino-2-propanol and 4-benzyloxy-indole-2-carbonyl chloride | 62 | 205–207 (ethanol) |
| (e) | 1-isopropylamino-3-[4-(5-methoxy-indole-2-carboxamido)-phenoxy]-2-propanol from 1-(4-amino-phenoxy)-3-isopropylamino-2-propanol and 5-methoxy-indole-2-carbonyl chloride | 75 | 165–167 (isopropanol) |
| (f) | 1-[4-(4,5-dimethylindole-2-carboxamido)phenoxy]-3-isopropylamino-2-propanol from 1-(4-aminophenoxy)-3-isopropylamino-2-propanol and 4,5-dimethyl-indole-2-carbonyl chloride | 95 | 175–177 (ethanol) |
| (g) | 1-isopropylamino-3-[4-(5-methoxy-4-methyl-indole-2-carboxamido)-phenoxy]-2-propanol from 1-(4-aminophenoxy)-3-isopropyl-amino-2-propanol and 5-methoxy-4-methylindole-2-carbonyl chloride | 76 | 205–207 (ethanol) |
| (h) | 1-[4-(6-hydroxypyridine-2-carboxamido)phenoxy]-3-isopropylamino-2-propanol hydrochloride from 1-(4-aminophenoxy)-3-N—benzyl-isopropylamino-2-propanol and 6-hydroxypyridine-2-carbonyl chloride | 69 | 189–192 (ethanol) |
| (i) | 1-[4-(5-bromo-2-methoxy-nicotinoylamido)-phenoxy]-3-isopropylamino-2-propanol hydrochloride from 1-(4-aminophenoxy-3-isopropyl-amino-2-propanol and 5-bromo-2-methoxynicotinic acid chloride | 50 | 212–214 (acetone) |
| (j) | 1-[4-(7-chloroindole-2-carboxamido)phenoxy]-3-isopropylamino-2-propanol from 1-(4-aminophenoxy)-3-isopropyl-amino-2-propanol and 7-chloro-indole-2-carbonyl chloride | 72 | 165–168 (acetic ester) |
| (k) | 1-[4-benzimidazole-2-carboxamido)-phenoxy]-3-isopropylamino-2-propanol from 1-(4-aminophenoxy)-3-isopropyl-amino-2-propanol and benzimidazole-2-carbonyl chloride | 33 | 211–212 (dimethylformamide) |
| (l) | 1-[4-(quinoline-2-carboxamido)-phenoxy]-3-isopropylamino-2-propanol from 1-(4-aminophenoxy)-3-isopropyl-amino-2-propanol and quinoline-2-carbonyl chloride | 89 | 148–150 (isopropanol) |

Example 7
1-[2-acetyl-4-(indole-2-carboxamido)phenoxy]-3-isopropylamino-2-propanol A mixture of 10.0 g of 2-(2,3-epoxypropoxy)-5-(indole-2-carboxamido)acetophenone, 100 ml of ethanol and 75 ml of isopropylamine is refluxed for 24 hours, concentrated, and purified by column chromatography on silica gel, the eluent being a 4:1 mixture of dichloromethane and methanol.

3.7 g of the title compound (30% of the theory) is isolated, having a melting point of 190°–210° C. (as amorphous hydrochloride).

The 2-(2,3-epoxypropoxy)-5-(indole-2-carboxamido)acetophenone used as the starting substance can be obtained as follows: The reaction of 5-amino-2-hydroxyacetophenone with indole-2-carbonic acid chloride leads to 2-hydroxy-5-(indole-2-carboxamido)acetophenone with a melting point of 119° C., which is reacted with epichlorhydrin in the presence of sodium alcoholate to form the crude 2-(2,3-epoxypropoxy)-5-(indole-2-carboxamido)acetophenone.

Example 8

In a manner similar to that described in Example 7, the following are obtained:

| Name | Yield % | Melting Point °C. (solvent) |
|---|---|---|
| (a) 1-[1,1-dimethyl-2-(4-hydroxyphenyl)ethylamino]-3-[4-(indole-2-carboxamido)phenoxy]-2-propanol from | 44 | 150–152 (acetone) |
| N—[4-(2,3-epoxypropoxy)phenyl]-indole-2-carboxamide and 1,1-dimethyl-2-(4-hydroxyphenyl)ethylamine | | |
| (b) 1-[4-(indole-2-carboxamido)-phenoxy]-3-[1,1-dimethyl-2-(3-indolyl)ethylamino]-2-propoanol from | 37 | 153–155 (acetic ester) |
| N—[4-(2,3-epoxypropoxy)phenyl]-indole-2-carboxamide and 1,1-dimethyl-2-(3-indolyl)-ethylamine | | |
| (c) 1-[2-(2-allyloxyphenoxy)ethylamino]-3-[4-(indole-2-carboxamido)phenoxy]-2-propanol from | 40 | 146–147 (isopropanol) |
| N—[4-(2,3-epoxypropoxy)-phenyl]-indole-2-carboxamide and 2-(2-allyloxyphenoxy)ethylamine | | |

Example 9

1-[4-(indole-2-carboxamido)phenoxy]-3-isopropylamino-2-pivaloyloxypropane 4.6 g of 1-[4-(indole-2-carboxamido)phenoxy]-3-isopropylamino-2-propanol (free base of the compound of Example 1) is added to 30 g of melted pivalic acid and 6.3 g of pivalic acid anhydride is added. The mixture is stirred for 5 days at room temperature, then poured into 100 ml of ice water, neutralized with dilute ammonia (1:10), and extracted with dichloromethane, and the extract is concentrated. The title compound is obtained (88% of the theory) with a melting point of 138°–140° C.

Example 10

Tablets were prepared, each containing 10 mg of 1-[4-(indole-2-carboxamido)phenoxy]-3-isopropylamino-2-propanol hydrochloride. The tablets were prepared according to the following formula:

| | |
|---|---|
| 1-[4-(indole-2-carboxamido)-phenoxy]-3-isopropylamino-2-propanol hydrochloride | 10 g |
| lactose | 80 g |
| starch | 29 g |
| magnesium stearate | 1 g |

The above compound was finely pulverized and mixed with the lactose and starch. The mixture was granulated by a conventional method. Magnesium stearate was added to the granular product, and the mixture was pressed to form 1000 tablets each weighing 0.12 g.

It will be understood that the specification and examples are illustrative but not limitative of the present invention and that other embodiments within the spirit and scope of the invention will suggest themselves to those skilled in the art.

What is claimed is:

1. Aminopropanol compound of the formula

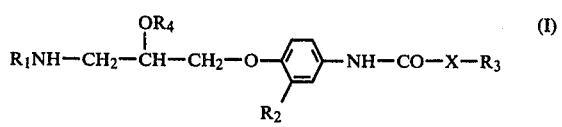

wherein $R_1$ is a lower alkyl or lower alkyl substituted by a group $Z$-$R_5$ $R_2$ is hydrogen or lower alkanoyl;

$R_3$ is unsubstituted pyridyl, pyrrolyl or indolyl, or monosubstituted wherein the substituents for these groups being selected from halogen, hydroxyl, lower alkoxy, or lower alkyl, $R_4$ is hydrogen, $R_5$ is hydrogen, X is a valence bond, Z is a valence bond, oxygen atom or sulfur atom.

2. Compound of claim 1 wherein $R_3$ is pyridyl.

3. Compound of claim 1 wherein $R_3$ is pyrrolyl.

4. Compound of claim 1 wherein $R_3$ is indolyl.

5. Compound of claim 1 wherein $R_1$ is substituted lower alkyl.

6. Compound of claim 1 wherein $R_2$ is hydrogen.

7. Compound of claim 1 wherein $R_2$ is lower alkanoyl.

8. Compound of claim 1 wherein Z is valence bond.

9. Compound of claim 1 wherein Z is oxygen.

10. Compound of claim 1 wherein Z is sulfur.

11. The aminopropanol compound as claimed in claim 1 which is designated 1-[4-(indole-2-carboxamido) phenoxy]-3-isopropylamino-2-propanol hydrochloride.

12. The aminopropanol compound as claimed in claim 1 which is designated 1-isopropylamino-3-[4-(pyrrole-2-carboxamido) phenoxy]-2-propanol.

13. The aminopropanol compound as claimed in claim 1 which is designated 1-isopropylamino-3[4-(pyridin-4-carboxamido)-phenoxy)]-2-propanol hydrochloride.

14. Pharmaceutical composition for the treatment and prophylaxis of tachycardia and angina pectoris comprising a pharmaceutically acceptable carrier and, in effective amounts, a aminopropanol compound as claimed in claim 1.

15. Composition as claimed in claim 14 wherein said compound is selected from

1-[4-(indole-2-carboxamido) phenoxy]-3-isopropylamino-2-propanol hydrochloride;

1-isopropylamino-3[4-(pyridin-4-carboxamido)-phenoxy)]-2-propanol hydrochloride; and 1-isopropylamino-3-[4-(pyrrole-2-carboxamido) phenoxy]-2-propanol.

16. Method of treating a subject for tachycardia and angina-pectoris which comprises administering to an afflicted subject, a pharmacologically effective amount of an aminopropanol compound as claimed in claim 1.

17. Method as claimed in claim 16 wherein the compound is applied at a dosage of 1.0 to 20 mg/kg daily.

18. Method as claimed in claim 16 wherein such compound is administered in a prophylactic manner.

19. Method as claimed in claim 16 wherein said circulatory and cardiac disease is tachycardia.

20. Method as claimed in claim 16 wherein said circulatory and cardiac disease is angina pectoris.

21. Method as claimed in claim 16 wherein said compound is selected from

1-[4-(indole-2-carboxamido) phenoxy]-3-isopropylamino-2-propanol hydrochloride;

1-isopropylamino-3[4-(pyridin-4-carboxamido)-phenoxy)]-2-propanol hydrochloride; and 1-isopropylamino-3-[4-(pyrrole-2-carboxamido) phenoxy]-2-propanol.

* * * * *